United States Patent [19]

Bellis

[11] Patent Number: 4,727,163

[45] Date of Patent: Feb. 23, 1988

[54] PROCESS FOR PREPARING HIGHLY PURE CYCLIC ESTERS

[75] Inventor: Harold E. Bellis, Wilmington, Del.

[73] Assignee: E. I. Du Pont de Nemours and Company, Wilmington, Del.

[21] Appl. No.: 925,484

[22] Filed: Oct. 29, 1986

Related U.S. Application Data

[63] Continuation-in-part of Ser. No. 753,907, Jul. 11, 1985, abandoned.

[51] Int. Cl.$^4$ ............................................. C07D 319/12
[52] U.S. Cl. ..................................................... 549/274
[58] Field of Search ........................................... 549/274

[56] References Cited

U.S. PATENT DOCUMENTS

| 2,163,109 | 6/1939 | Spanagel | 549/267 |
|---|---|---|---|
| 2,163,268 | 6/1939 | Carothers et al. | 260/338 |
| 2,668,162 | 2/1954 | Lowe | 260/78.3 |
| 3,435,008 | 3/1969 | Schmitt et al. | 260/78.3 |
| 3,442,871 | 5/1969 | Schmitt et al. | 549/274 |
| 3,457,280 | 7/1969 | Schmitt et al. | 260/340.2 |
| 3,763,190 | 10/1973 | Ross et al. | 260/340.2 |

FOREIGN PATENT DOCUMENTS 1108720  4/1968  United Kingdom ................. 549/274

OTHER PUBLICATIONS

Translation of Japanese Kokai Patent Publication No. 55-120,581, published Sep. 17, 1980.
J. W. Hill et al., Jour. Am. Chem. Soc., vol. 55 (1933), pp. 5031–5039.
J. W. Hill et al., Jour. Am. Chem. Soc., vol. 55 (1933), pp. 5039–5043.
W. H. Carothers et al., Jour. Am. Chem. Soc., vol. 55 (1933), pp. 5043–5052.

*Primary Examiner*—Norma S. Milestone
*Attorney, Agent, or Firm*—Craig H. Evans

[57] ABSTRACT

A process for making highly pure cyclic esters by heating a copolymer of $\alpha$-hydroxy acid or its ester on a thermally stable polyether core.

14 Claims, No Drawings

PROCESS FOR PREPARING HIGHLY PURE CYCLIC ESTERS

This application is a continuation-in-part of application Ser. No. 753,907 filed July 11, 1985, now abandoned.

DESCRIPTION OF THE INVENTION

Technical Field

This invention relates to highly pure cyclic esters and an improved process for preparing them by heating a copolymer of α-hydroxy acid or its ester and a thermally stable polyether. The cyclic ester can be separated from the reaction mixture by vacuum distillation, solvent extracted and purified by recrystallization. The thermally stable polyether residue can be recycled to make added copolymer with fresh α-hydroxy acid or its ester.

BACKGROUND AND SUMMARY OF THE INVENTION

Cyclic esters of the general formula

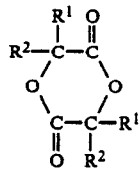

wherein $R^1$ and $R^2$ can be independently hydrogen or an aliphatic hydrocarbon having from 1 to about 6 carbon atoms, are a useful class of compounds that can be polymerized into high molecular weight polymeric plastic materials particularly useful in medical applications such as wound closure devices, orthopedic implants, and controlled release drug carriers.

In the past, these cyclic esters have been prepared by first making a brittle, polymeric form of the α-hydroxy acid corresponding to the cyclic ester. For example, if the desired product was glycolide, glycolic acid would be converted to a brittle polymeric form of polyglycolic acid. The polymeric material would then be ground to a fine powder and added slowly to a heated, evacuated vessel in which it would be thoroughly depolymerized to a crude material which had to be subjected to an extensive and costly purification operation. This process suffered from excessive tar formation, low yields, and slow production rates. One attempt to improve upon that thermal cracking process and to prepare relatively pure glycolide is described in U.S. Pat. No. 3,763,190 to Donald L. Ross. That process required first making a salt of an O-haloacetylglycolic acid and then heating the salt to a sufficient temperature to effect ring closure. Mineral salts had to be removed and the resulting glycolide separated and purified by sublimation.

The process of the present invention is a thermal cracking process that does not involve formation of a salt of a halogenated α-hydroxy acid. The present invention is distinguished from past thermal cracking processes such as the one described above in that excessive tar formation is avoided, yields are substantially higher, reaction rates are much faster, and as a result of low tar formation, the process can be run continuously, as well as batchwise.

The process of this invention involves first making a block polymer comprising a thermally stable polyether core with α-hydroxy acid or its ester polymerized onto the ends of the core. Upon heating under vacuum conditions, the chain ends are thermally degraded to form a cyclic ester which can be condensed under vacuum leaving behind any water or alcohol and tar formed in the residual thermally stable polyether which can be recycled to make added copolymer with fresh α-hydroxy acid or its ester. The copolymer can then be thermally decomposed to evolve added cyclic esters. The crude cyclic ester can then be solvent extracted and recrystallized to form a highly pure product.

The product of the present invention is purer than the product of other heretofore known processes.

DETAILED DESCRIPTION OF THE INVENTION

The process of this invention requires initially forming a block copolymer of a thermally stable polyether core with an α-hydroxy acid or its ester polymerized on each end of the core. The thermally stable polyether may be aliphatic or aromatic. The preferred aliphatic polyether is a polyether glycol such as Teracol ®, manufactured by E. I. du Pont de Nemours and Company. The polyether glycol may have a wide range of molecular weights. Teracol ®, for example, is commercially available in molecular weights ranging from 650 to 2900. Higher molecular weights can be made. Polyether glycols having lower molecular weights than Teracol ® may be used. The preferred molecular weight ranges from about 900 to 3000. The most preferred is in the range of about 1800 to 2200. The preferred aromatic polyether is a phenylene oxide. The α-hydroxy acid is of the form $R^1R^2C(OH)COOH$, wherein $R^1$ and $R^2$ can be independently hydrogen or aliphatic hydrocarbon groups having from 1 to 6 carbons. The preferred α-hydroxy acids are glycolic acid and lactic acid. The ester of the α-hydroxy acid is of the form $R^1R^2C(OH)COOR^3$, wherein $R^1$ and $R^2$ are defined as for the α-hydroxy acid and $R^3$ is an aliphatic hydrocarbon group having from 1 to 6 carbons. The preferred esters are methyl and ethyl glycolate and methyl and ethyl lactate.

The block copolymer of the thermally stable polyether and the α-hydroxy acid, hereinafter referred to as prepolymer, can be made by heating the α-hydroxy acid or its ester and the thermally stable polyether core in the presence of a polymerization catalyst, preferably one that is neutral or basic. Also, a nonvolatile base such as, but not limited to, an alkaline earth oxide may be added. For example, to make the prepolymer, Teracol ® glycolic acid, glycolic acid and Teracol ® can be heated at a temperature of 175° to 225° C. and a pressure of 25 to 250 mm of mercury in the presence of antimony trioxide. The prepolymer is formed under these conditions evolving water and some tetrahydrofuran (THF).

The prepolymer temperature is raised to a sufficiently high temperature to thermally degrade the α-hydroxy acid or its ester ends. This depolymerization is carried out in a vacuum and the crude cyclic ester that evolves is condensed and collected. Suitable temperatures for this depolymerization range from about 225° to 285° C. with the preferred temperature range being from about 235° to 265° C. The vacuum under which this step is carried out ranges from about 1 to 25 mm of mercury and preferably from about 2 to 10 mm of mercury. This step also can be run in the presence of a nonvolatile base.

The crude cyclic ester evolved can be solvent extracted and recrystallized to achieve high purity. The residue polyether can be reused to make additional prepolymer.

Since tar formation is minimized by the process of the instant invention and since the residue polyether can be recycled, the process of this invention can be run continuously as well as batchwise. In the continuous process the residue polyether is recycled to make additional prepolymer. The minimal tars that are formed in the depolymerization are soluble in the solvent that evolves during manufacture of the prepolymer and thus tar levels can be controlled to avoid build-up in the system.

By minimizing tar formation, the process permits production of a purer cyclic ester of the form

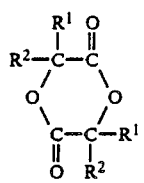

wherein $R^1$ and $R^2$ can be independently hydrogen or an aliphatic hydrocarbon having from 1 to about 6 carbon atoms, than has been produced heretofor.

In order that the concept of the present invention may be more fully understood, the following examples are set forth. They are intended for illustration and not limitation.

EXAMPLE 1

Preparation of Glycolide by Thermal Decomposition Of a Teracol ®-hydroxyacetic Acid Block Polymer Two hundred (200) grams of recrystallized hydroxyacetic acid (HAA) was added to 400 grams of Teracol ®-1000 (MW=1000) and 0.05 gram antimony trioxide. This mixture was copolymerized by treatment at 200° C. and 223 mm Hg to yield a prepolymer and to remove 32 grams of liquid (about 20% THF and 80% water evolved). The temperature of 417.2 grams of the resulting prepolymer was then raised to 280° C. and vacuum increased to 7 mm Hg and, over the next hour, 102.9 grams crude glycolide was collected. The reactor was run another two hours and an additional 25.5 grams crude glycolide was collected. An additional 11.8 grams of crude glycolide was collected in a trap. A portion of the crude glycolide (10.2 grams) was recrystallized twice from ethyl acetate yielding a product consisting of 8.55 grams refined glycolide. A melting point determination indicated a 99+% purity.

EXAMPLE 2

Reuse of Teracol ® to Produce Glycolide

Two hundred fifty four (254) grams of heel from Example 1, was blended with 150 grams of fresh recrystallized HAA. The copolymerization step was repeated at 165° C. and 140 mm Hg to yield added prepolymer and to remove 21 grams (8% THF, 91% water). This prepolymer was next heated at 250° C. and 4 mm Hg and 96 grams crude glycolide was recovered. A portion of this crude product (10.2 grams) was then recrystallized twice from ethyl acetate and yielded 8.52 grams refined glycolide. A melting point determination indicated a 99+% purity.

EXAMPLE 3

Preparation of Glycolide by Known Chemistry

One hundred (100) grams anhydrous HAA was polymerized in the presence of 1 gram antimony trioxide at 192° C. and 12 mm Hg vacuum. Product was ground to a fine powder which was added slowly (over two hours) to a heated vessel at 222° C. and 8 mm Hg vacuum. Crude glycolide was obtained in amount of 6.9 grams from about 34.3 grams fine powder fed. The crude product was twice recrystallized from ethyl acetate to yield 4.1 grams refined glycolide. The reactor walls were badly charred by nonconverted HAA feed. A melting point determination indicated a purity of about 90%.

EXAMPLE 4

Preparation of Glycolide by Other Teracol ®

Two hundred (200) grams anhydrous HAA and 400 grams Teracol ®-1800 (MW=1800) were heated with 0.05 grams antimony trioxide at 215° C. and 4 mm Hg over a period of 3 hours until liquid evolution ceasell. A total of 333 cc. liquid (75% THF, 25% water) was removed. The prepolymer was then heated to 270° C. under 10 mm Hg and 88 grams crude glycolide was produced. The heel of Teracol ® amounted to 165 grams. The crude product was recrystallized twice from ethyl acetate yielding 75 grams refined glycolide. The IR spectra agreed with published literature and a TGA indicated 99+% purity. The C, H analysis was 41.6% C and 3.6% H (41.4 and 3.4 theory).

I claim:

1. A process for making a cyclic ester of the formula

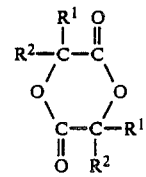

wherein $R^1$ and $R^2$ can be independently hydrogen or an aliphatic hydrocarbon having from 1 to about 6 carbon atoms, the process comprising:
   a. forming a block copolymer of a thermally stable polyether core with a corresponding α-hydroxy acid or its ester on each end of the core, and then
   b. thermally degrading the ends at a suitable temperature and vacuum to evolve the cyclic ester and leave a thermally stable polyether residue.

2. The process of claim 1 wherein the thermally stable polyether core is an aliphatic polyether.

3. The process of claim 2 wherein the aliphatic polyether is a polyether glycol.

4. The process of claim 3 wherein the polyether glycol has a molecular weight of between 900 and 3000.

5. The process of claim 3 wherein the polyether glycol has a molecular weight of between 1800 and 2200.

6. The process of claim 1 wherein the thermally stable polyether core is an aromatic polyether.

7. The process of claim 6 wherein the aromatic polyether is a phenylene oxide.

8. The process of claim 1 wherein the α-hydroxy acid is glycolic acid or lactic acid.

9. The process of claim 1 wherein the ester of α-hydroxy acid is methyl or ethyl glycolate or methyl or ethyl lactate.

10. The process of claim 1 wherein the temperature in step b is from about 225° to 285° C. and the vacuum is from about 1 to 25 mm mercury.

11. the process of claim 1 further comprising the addition of a nonvolatile base during step a or step b.

12. The process of claim 1 or claim 11 further comprising the added steps of dissolving the cyclic ester in a solvent and recrystallizing the cyclic ester from the solvent.

13. The process of claim 12 wherein the solvent is dry ethyl acetate.

14. The process of claim 1 or claim 11 further comprising the added step of recyling the thermally stable polyether residue of claim 1, step b, to claim 1, step a.

* * * * *